United States Patent
Murphy et al.

(10) Patent No.: US 7,485,088 B2
(45) Date of Patent: *Feb. 3, 2009

(54) METHOD AND DEVICE FOR PERCUTANEOUS SURGICAL VENTRICULAR REPAIR

(75) Inventors: Gregory Murphy, Richardson, TX (US); Mitta Suresh, Richardson, TX (US); Albert Davis, Richardson, TX (US)

(73) Assignee: Chase Medical L.P., Richardson, TX (US)

( * ) Notice: Subject to any disclaimer, the term of this patent is extended or adjusted under 35 U.S.C. 154(b) by 714 days.

This patent is subject to a terminal disclaimer.

(21) Appl. No.: 10/235,295

(22) Filed: Sep. 5, 2002

(65) Prior Publication Data

US 2004/0249408 A1 Dec. 9, 2004

Related U.S. Application Data

(60) Provisional application No. 60/317,197, filed on Sep. 5, 2001, provisional application No. 60/327,221, filed on Oct. 5, 2001.

(51) Int. Cl.
*A61F 2/00* (2006.01)
*A61F 13/00* (2006.01)
(52) U.S. Cl. .................................. 600/37; 623/3.1
(58) Field of Classification Search ......... 606/191–198; 128/898; 600/16, 587, 37; 623/3.1, 23.72; 601/153

See application file for complete search history.

(56) References Cited

U.S. PATENT DOCUMENTS 2,701,559 A 2/1955 Cooper
3,568,659 A 3/1971 Karnegis
3,874,388 A 4/1975 King et al.
3,983,863 A 10/1976 Janke et al.
4,685,446 A 8/1987 Choy
4,690,134 A 9/1987 Snyders
4,718,135 A 1/1988 Colvin
4,771,765 A 9/1988 Choy et al.
4,785,795 A 11/1988 Singh
4,817,637 A 4/1989 Hillegass et al.

(Continued)

FOREIGN PATENT DOCUMENTS

DE 29911694 8/1999

(Continued)

OTHER PUBLICATIONS

International Search Report PCT/US02/16304 mailed Aug. 22, 2002.

(Continued)

*Primary Examiner*—Melanie Tyson
(74) *Attorney, Agent, or Firm*—Meyertons, Hood, Kivlin, Kowert & Goetzel, P.C.; Eric B. Meyertons

(57) ABSTRACT

In one embodiment, there is disclosed a method for repairing a heart of a human, comprising introducing a collapsed shaping device through the skin into the vascular system of the human, delivering the shaping device into a left ventricle through the arteries, once inside the left ventricle, expanding the shaping device to an expanded shape, imbricating a wall of the ventricle over the shaping device, collapsing the shaping device, and removing the shaping device from the left ventricle such that the ventricle is restored to an appropriate size.

23 Claims, 14 Drawing Sheets

U.S. PATENT DOCUMENTS

| | | | |
|---|---|---|---|
| 4,819,751 A * | 4/1989 | Shimada et al. | 606/194 |
| 4,821,723 A | 4/1989 | Baker, Jr. et al. | |
| 4,861,330 A | 8/1989 | Voss | |
| 4,902,273 A | 2/1990 | Choy et al. | |
| 4,917,089 A | 4/1990 | Sideris | |
| 4,938,231 A | 7/1990 | Milijasevic et al. | |
| 4,957,477 A | 9/1990 | Lundback | |
| 4,973,300 A | 11/1990 | Wright | |
| 5,041,130 A | 8/1991 | Cosgrove et al. | |
| 5,089,005 A | 2/1992 | Harada | |
| 5,092,879 A | 3/1992 | Jarvik | |
| 5,131,905 A | 7/1992 | Grooters | |
| 5,139,517 A | 8/1992 | Corral | |
| 5,156,151 A | 10/1992 | Imran | |
| 5,167,628 A | 12/1992 | Boyles | |
| 5,169,378 A | 12/1992 | Figuera | |
| 5,171,299 A | 12/1992 | Heitzmann et al. | |
| 5,176,619 A | 1/1993 | Segalowitz | |
| 5,192,314 A | 3/1993 | Daskalakis | |
| 5,255,678 A | 10/1993 | Deslauriers et al. | |
| 5,258,000 A | 11/1993 | Gianturco | |
| 5,334,146 A | 8/1994 | Ozasa | |
| 5,409,000 A | 4/1995 | Imran | |
| 5,411,527 A | 5/1995 | Alt | |
| 5,425,744 A | 6/1995 | Fagan et al. | |
| 5,433,727 A | 7/1995 | Sideris | |
| 5,451,235 A | 9/1995 | Lock et al. | |
| 5,465,717 A | 11/1995 | Imran et al. | |
| 5,489,296 A | 2/1996 | Love et al. | |
| 5,507,811 A | 4/1996 | Koike et al. | |
| 5,509,428 A | 4/1996 | Dunlop | |
| 5,526,810 A | 6/1996 | Wang | |
| 5,603,337 A | 2/1997 | Jarvik | |
| 5,609,157 A | 3/1997 | Panescu et al. | |
| 5,632,776 A | 5/1997 | Kurumatani et al. | |
| 5,702,343 A | 12/1997 | Alferness | |
| 5,713,950 A | 2/1998 | Cox | |
| 5,722,401 A | 3/1998 | Pietroski et al. | |
| 5,725,552 A | 3/1998 | Kotula et al. | |
| 5,738,626 A | 4/1998 | Jarvik | |
| 5,749,839 A | 5/1998 | Kovacs | |
| 5,758,664 A * | 6/1998 | Campbell et al. | 128/898 |
| 5,797,960 A | 8/1998 | Stevens et al. | |
| 5,800,528 A | 9/1998 | Lederman et al. | |
| 5,814,098 A | 9/1998 | Hinnenkamp et al. | |
| 5,843,177 A | 12/1998 | Vanney et al. | |
| 5,846,260 A | 12/1998 | Maahs | |
| 5,846,261 A | 12/1998 | Kotula et al. | |
| 5,868,779 A | 2/1999 | Ruiz | |
| 5,885,228 A | 3/1999 | Rosenman et al. | |
| 5,904,680 A | 5/1999 | Kordis et al. | |
| 5,908,445 A | 6/1999 | Whayne et al. | |
| 5,910,124 A | 6/1999 | Rubin | |
| 5,921,935 A | 7/1999 | Hickey | |
| 5,923,770 A | 7/1999 | O'Donnell et al. | |
| 5,944,738 A | 8/1999 | Amplatz et al. | |
| 5,951,543 A | 9/1999 | Brauer | |
| 5,957,977 A | 9/1999 | Melvin | |
| 5,964,806 A | 10/1999 | Cook et al. | |
| 5,971,911 A | 10/1999 | Wilk | |
| 6,004,329 A | 12/1999 | Myers et al. | |
| 6,019,739 A | 2/2000 | Rhee et al. | |
| 6,024,096 A | 2/2000 | Buckberg | |
| 6,077,214 A | 6/2000 | Mortier et al. | |
| 6,099,832 A | 8/2000 | Mickle et al. | |
| 6,109,852 A | 8/2000 | Shahinpoor et al. | |
| 6,123,715 A | 9/2000 | Amplatz | |
| 6,125,852 A | 10/2000 | Stevens et al. | |
| 6,143,012 A | 11/2000 | Gausepohl | |
| 6,152,144 A | 11/2000 | Lesh et al. | |
| 6,162,168 A | 12/2000 | Schweich, Jr. et al. | |
| 6,162,537 A | 12/2000 | Martin et al. | |
| 6,179,791 B1 | 1/2001 | Krueger | |
| 6,183,411 B1 | 2/2001 | Mortier et al. | |
| 6,205,411 B1 | 3/2001 | DiGioia, III et al. | |
| 6,210,338 B1 | 4/2001 | Afremov et al. | |
| 6,216,043 B1 | 4/2001 | Swanson et al. | |
| 6,221,104 B1 | 4/2001 | Buckberg et al. | |
| 6,231,601 B1 | 5/2001 | Myers et al. | |
| 6,261,832 B1 | 7/2001 | Law | |
| 6,322,588 B1 | 11/2001 | Ogle et al. | |
| 6,350,281 B1 | 2/2002 | Rhee | |
| 6,360,749 B1 | 3/2002 | Jayaraman | |
| 6,366,684 B1 | 4/2002 | Gerard et al. | |
| 6,368,356 B1 | 4/2002 | Zhong et al. | |
| 6,406,420 B1 | 6/2002 | McCarthy et al. | |
| 6,419,669 B1 | 7/2002 | Frazier et al. | |
| 6,439,237 B1 | 8/2002 | Buckberg et al. | |
| 6,450,171 B1 | 9/2002 | Buckberg et al. | |
| 6,529,756 B1 | 3/2003 | Phan et al. | |
| 6,544,167 B2 | 4/2003 | Buckberg et al. | |
| 6,551,303 B1 | 4/2003 | Van Tassel et al. | |
| 6,652,556 B1 | 11/2003 | Van Tassel et al. | |
| 6,681,773 B2 | 1/2004 | Murphy et al. | |
| 6,702,763 B2 | 3/2004 | Murphy et al. | |
| 6,726,696 B1 | 4/2004 | Houser | |
| 6,852,076 B2 | 2/2005 | Nikolic et al. | |
| 6,887,192 B1 | 5/2005 | Whayne et al. | |
| 6,959,711 B2 | 11/2005 | Murphy et al. | |
| 6,994,093 B2 | 2/2006 | Murphy et al. | |
| 2002/0026092 A1 | 2/2002 | Buckberg et al. | |
| 2002/0029783 A1 | 3/2002 | Stevens et al. | |
| 2002/0056461 A1 | 5/2002 | Jayaraman | |
| 2002/0111647 A1 | 8/2002 | Khairkhahan et al. | |
| 2002/0133143 A1 | 9/2002 | Murphy et al. | |
| 2002/0133227 A1 | 9/2002 | Murphy et al. | |
| 2002/0143362 A1 | 10/2002 | Macoviak et al. | |
| 2003/0045896 A1 | 3/2003 | Murphy et al. | |
| 2003/0050659 A1 | 3/2003 | Murphy et al. | |
| 2003/0050682 A1 | 3/2003 | Sharkey et al. | |
| 2003/0050685 A1 | 3/2003 | Nikolic et al. | |
| 2003/0105384 A1 | 6/2003 | Sharkey et al. | |
| 2003/0109770 A1 | 6/2003 | Sharkey et al. | |
| 2003/0125604 A1 | 7/2003 | Kochamba et al. | |
| 2003/0158570 A1 | 8/2003 | Ferrazzi | |
| 2003/0163191 A1 | 8/2003 | Nikolic et al. | |
| 2003/0181940 A1 | 9/2003 | Murphy et al. | |
| 2003/0192561 A1 | 10/2003 | Murphy et al. | |
| 2004/0243170 A1 | 12/2004 | Murphy et al. | |
| 2005/0015109 A1 | 1/2005 | Lichtenstein | |
| 2005/0096498 A1 | 5/2005 | Houser et al. | |
| 2005/0278024 A1 | 12/2005 | Murphy et al. | |
| 2006/0025800 A1 | 2/2006 | Murphy et al. | |
| 2006/0247764 A1 | 11/2006 | Annest et al. | |

FOREIGN PATENT DOCUMENTS

| | | |
|---|---|---|
| EP | 1474032 | 11/2004 |
| RU | 2107467 | 3/1998 |
| WO | 95/18593 | 7/1995 |
| WO | 99/03973 | 1/1999 |
| WO | 99/56655 | 11/1999 |
| WO | 02/19917 A1 | 3/2002 |
| WO | 03/061455 | 7/2003 |
| WO | 2005094729 | 10/2005 |

OTHER PUBLICATIONS

Marisa Di Donato et al., "Effects of the Dor Procedure on Left Ventricular Dimension and Shape and Geometric Correlates of Mitral Regurgitation One year After Surgery" *The Journal of Thoracic and Cardiovascular Surgery*, Jan. 2001, 91-96.

Hisayoshi Suma et al., "Nontransplant Cardiac Surgery For End-Stage Cardiomyopathy" *The Journal of Thoracic and Cardiovascular Surgery*, 2000, Jun, 1233-1245.

Rufus Baretti et al., "Batista Procedure: Elliptical Modeling Against Spherical Distention" *European Journal of Cardio-Thoracic Surgery*, 2000, 17, 52-57.

Randas Batista, "Partial Left Ventriculectomy—The Batista Procedure" *European Journal of Cardio-Thoracic Surgery*, 1999, 15, S12-S19.

Gerald D. Buckberg, M.D., "Commonality of Ischemic and Dilated Cardiomyopathy: Laplace and Ventricular Restoration" The UCLA Medical Center, Department of Surgery, Los Angeles, California, 1999, 53-59.

F. Fantini et al., "Effects of Reconstructive Surgery For Left Ventricular Anterior Aneurysm on Ventriculoarterial Coupling" *Heart*, 1999, 81, 171-176.

V. Dor et al., "Endoventricular Patch Reconstruction in Large Ischemic Wall-Motion Abnormalities" *The Centre Cardio-Thoracique*, Monaco, 1999, 46-52.

Randall C. Starling and Patrick M. McCarthy, "Partial Left Ventriculectomy: Sunrise or Sunset?" *European Journal of Heart Failure*, 1999, 1, 313-317.

V.Dor et al., "Endoventricular Patch Plasty for Large L.V. Akinesia" Videotape from *Centre de Cardio-Thoracique de Monaco*, 1998, Sep.

Gerald D. Buckberg, M.D., "Surgery for Adult Cardiovascular Disease: Editorial: Defining the Relationship Between Akinesia and Dyskinesia and the Cause of Left Ventricular Failure After Anterior Infraction and Reversal of Remodeling to Restoration" 1998, 116, 47-49.

Sakamoto et al. "Restoring the Remodeled Enlarged Left Ventricle: Experimental Benefits of In Vivo Porcine Cardioreduction in the Beating Open Heart" Department Cardiology, UCLS School of Medicine, 1998, 429-439.

Athanasuleas, M.D. et al., "Restoration of Contractile Function in the Enlarged Left Ventricle by Exclusion of Remodeled Akinetic Anterior Segment: Surgical Strategy, Myocardial Protection, and Angiographic Results" *Journal of Cardiovascular Surgery*, 1998, 418-428.

V.Dor, M.D. et al. "Endoventricular Patch Plastics with Septal Exclusion for Repair of Ischemic Left Ventricle: Technique, Results and Indications from A Series of 781 Cases" *The Japanese Journal of Thoracic and Cardiovascular Surgery*, 1998, 389-398.

V. Dor, M.D. et al. "Ventricular Remodeling in Coronary Artery Disease" *Centre Cardio-Thoracique de Monaco*, 1997, 533-537.

Di Donato, M.D. et al., "Akinetic Versus Dyskinetic Postinfarction Scar: Relation to Surgical Outcome in Patients Undergoing Endoventricular Circular Patch Plasty Repair" *Journal of American College of Cardiology*, 1997, 29, 1569-1575.

Vincent Dor, "The Treatment of Refractory Ischemic Ventricular Tachycardia by Endoventricular Patch Plasty Reconstruction of the Left Ventricle" *Seminars in Thoracic and Cardiovascular Surgery*, Apr. 1997, 2, 2, 146-155.

Vincent Dor, "Reconstructive left Ventricular Surgery for Post-Ischemic Akinetic Dilation" *Seminars in Thoracic and Cardiovascular Surgery*, Apr. 1997, 9, 2, 139-145.

Vincent Dor, "Left Ventricular Aneurysms: The Endoventricular Circular Patch Plasty" *Seminars in Thoracic and Cardiovascular Surgery*, Apr. 1997, 9, 2, 123-130.

James L. Cox, Vincent Dor, "Surgical Management of Left Ventricular Aneurysms: A Clarification of the Similarities and Differences Between the Jetene and Dor Techniques" *Seminars in Thoracic and Cardiovascular Surgery*, Apr. 1997, 9, 2, 131-138.

Di Donato et al., "Outcome of Left Ventricular Aneurysmectomy with Patch Repair in Patients with Severely Depressed Pump Function" *The American Journal of Cardiology*, Sep. 15, 1995, 76, 557-561.

V. Dor et al., "Surgery For Acquired Heart Disease, Late Hemodynamic Results After Left Ventricular Patch Repair Association with Coronary Grafting in Patients with Postinfarcation akinetic or Dyskinetic Aneurysm of the Left Ventricle" *The Journal of Thoracic and Cardiovascular Surgery*, Nov. 1995, 1291-1301.

Elefteriades et al., "Left Ventricular Aneurysmetctomy in Advanced Left Ventricular Dysfunction" *Cardiology Clinics*, Feb. 1995, 13, 1, 59-72.

V. Dor et al., "Left Ventricular Shape Changes Induced by Aneurysmectomy with Endoventricular Circular Patch Plasty Reconstruction" *The European Society of Cardiology*, 1994, 1063-1069.

Cooley, M.D. et al., "Intracavitary Repair of Ventricular Aneurysm and Regional Dyskinesia" Departments of Cardiovascular Surgery and Cardiology, Texas Heart Institute, Houston, TX, May 1992, 417-424-890.

Di Donato et al., "Early Hemodynamic Results of Left Ventricular Reconstructive Surgery for Anterior Walls Left Ventricular Aneursym" *The American Journal of Cardiology*, 69, Apr. 1, 1992, 886-890.

Francis Fontan, M.D., "Transplantation of Knowledge" *The Journal Thoracic and Cardiovascular Surgery*, 1990, 387-395.

Denton A. Cooley, M.D., "Left Ventricular Endoaneurysmorrhaphy: A Simplified Repair for Extensive Postinfarction Aneurysm" *Journal of Cardiac Surgery*, 1989, 4, 3, 200-205.

V. Dor et al., "Ventricular Aneurysm: A New Surgical Approach" *Thorac. Cardiovasc. Surgeon*, 37, Jun. 16, 1989, 11-19.

T. Shiga et al. "Deformation of Polyelectrolyte Gets under the Influence of Electric Field" *Journal of Applied Polymer Science*, 1990,39, 2305.

J. Bohm et al. "Endoventricular Patch Plasty for Restoration of Ventricular Geometry and Pump Function in Ventricular Aneurysm" *Z. Kardiol*, 1996, 85, Supplement No. 4, 43-46.

A. D. Jatene, "Left Ventricular aneurysmectomy: Resection or reconstruction" *The Journal of Thoracic and Cardiovascular Surgery*, 1985, 89, 321-331.

K. Emmrich, "Contribution to the Discussion of the Lecture by J. Bohm, Berlin" *Z. Kardiol*, 1996, 85, Supplement No. 4, 47-48.

T. Kono et al., "Left Ventricular Shape Is the Primary Determinant of Functional Mitral Regurgitation in Heart Failure" *JACC*, Dec. 1992, vol. 20, No. 7, p. 1594-1598.

G. E. Burch et al., "Angle of traction of the papillary muscle in normal and dilated hearts: A theoretic analysis of its importance in mitral valve dynamics" *American Heart Journal*, Jul. 1972, vol. 84, No. 1, p. 141-144.

G. D. Buckberg, "Congestive Heart Failure: Treat the Disease, Not the Symptom—Return to Normalcy" *J Thorac Cardiovasc Surg*, 2001, vol. 121, No. 4, p. 628-637.

C. L. Anthanasuleas et al., "Surgical Anterior Ventricular Endocardial Restoration (SAVER) in the Dilated Remodeled Ventricle After Anterior Myocardial Infarction" *Journal of the American College of Cardiology*, 2001, vol. 37, No. 5, p. 1199-1209.

R. E. Michler et al., "Minimally Invasive Mitral Valve Replacement and Multivessel Coronary Artery Bypass Through a Limited Right Lateral Thoracotomy using a Balloon Aortic Cannula" The Heart Surgery Forum, 2001, vol. 5, No. 1, p. 49-51.

V. Dor, "Left ventricular restoration by endoventricular circular patch plasty (EVCPP)" Z. Kardiol, 2000, vol. 89, Suppl. 7, p. VII/70-VII/75.

V. Dor, M.D. et al. "Ventricular Remodeling in Coronary Artery Disease" Current Opinion in Cardiology, 1997, vol. 12, 533-537.

V. Dor et al., "Endoventricular Patch Reconstruction in Large Ischemic Wall-Motion Abnormalities" J. Card Surg, 1999, 14, 46-52.

International Search Report for EP 02729297 mailed May 19, 2004.

Di Donato, M. et al. "Regional Myocardial performance of non-ischaemic zones remote from anterior wall left ventricular aneurysm—Effects of aneurysmectomy", European Heart Journal, (1995) 16, 1285-1292.

Interview Summary for U.S. Appl. No. 09/864,794 mailed on Jul. 14, 2003.

Office Action for U.S. Appl. No. 09/864,510 mailed on Nov. 8, 2002.

Office Action for U.S. Appl. No. 09/864,510 mailed on May 7, 2003.

Office Action for U.S. Appl. No. 09/864,510 mailed on Feb. 19, 2004.

Interview Summary for U.S. Appl. No. 09/864,510 mailed on Mar. 17, 2004.

Office Action for U.S. Appl. No. 09/864,510 mailed on Aug. 26, 2004.

Advisory Action for U.S. Appl. No. 09/864,510 mailed on Dec. 3, 2004.

Written Opinion for PCT/US02/16304 mailed May 27, 2003.

International Preliminary Examination Report for PCT/US02/16304 mailed Jul. 15, 2004.
Office Action for U.S. Appl. No. 10/210,737 mailed on Jun. 30, 2004.
International Search Report and Written Opinion for PCT/US04/06061 mailed Oct. 8, 2004.
Office Action for U.S. Appl. No. 10/454,978 mailed on Sep. 27, 2004.
Office Action for U.S. Appl. No. 09/864,510 mailed on Mar. 23, 2005.
International Preliminary Examination Report for PCT/US02/16304 mailed Mar. 29, 2005.
International Preliminary Report on Patentability for PCT/US04/06061 mailed Apr. 1, 2005.
Interview Summary for U.S. Appl. No. 09/864,510 mailed on May 6, 2005.
Patent Appl. No. 11/158,293 mailed on Jun. 21, 2005 including current claims.
Communication Pursuant to Article 96(2) EPC for EP 0272929297.8 mailed Mar. 8, 2006.
Office Action for U.S. Appl. No. 10/350,297 mailed on Mar. 16, 2006.
International Search Report and Written Opinion for PCT/US06/01159 mailed Jun. 23, 2006.
DD01—Fantini, F. et al. "Quantitative Evaluation of Left Ventricular Shape in Anterior Aneurysm" Catheterization and Cardiovascular Diagnosis 1993, vol. 28, 295-300.
DD02—Di Donato, M. et al. "Akinetic Versus Dyskinetic Postinfarction Scar: Relation to Surgical Outcome in Patients Undergoing Endovascular Circular Patch Plasty Repair" Journal of American College of Cardiology, vol. 29, No. 7, Jun. 1997, 1569-1575.
DD03—Dor, V. "Results of nonguided subtotal endocardiectomy associated with left ventricular reconstruction in patients with ischemic ventricular arrhythmias" Journal of Thoracic and Cardiovascular Surgery, vol. 107, No. 5, May 1994, 1301-1308.
Office Action for U.S. Appl. No. 11/244,865 mailed on Oct. 9, 2007, available in PAIR.
Office Action for U.S. Appl. No. 11/244,865 mailed on Jan. 17, 2004, available in PAIR.
Office Action for U.S. Appl. No. 11/113,116 mailed on Jul. 2, 2007, available in PAIR.
Office Action for U.S. Appl. No. 10/350,297 mailed on Nov. 29, 2006, available in PAIR.
Office Action for U.S. Appl. No. 10/350,297 mailed on Jul. 2, 2007, available in PAIR.
Office Action for U.S. Appl. No. 10/790,669 mailed on Nov. 7, 2006, available in PAIR.
Office Action for U.S. Appl. No. 10/790,669 mailed on Aug. 13, 2007, available in PAIR.
Office Action for U.S. Appl. No. 10/350,297 mailed on Apr. 25, 2008, available in PAIR.

* cited by examiner

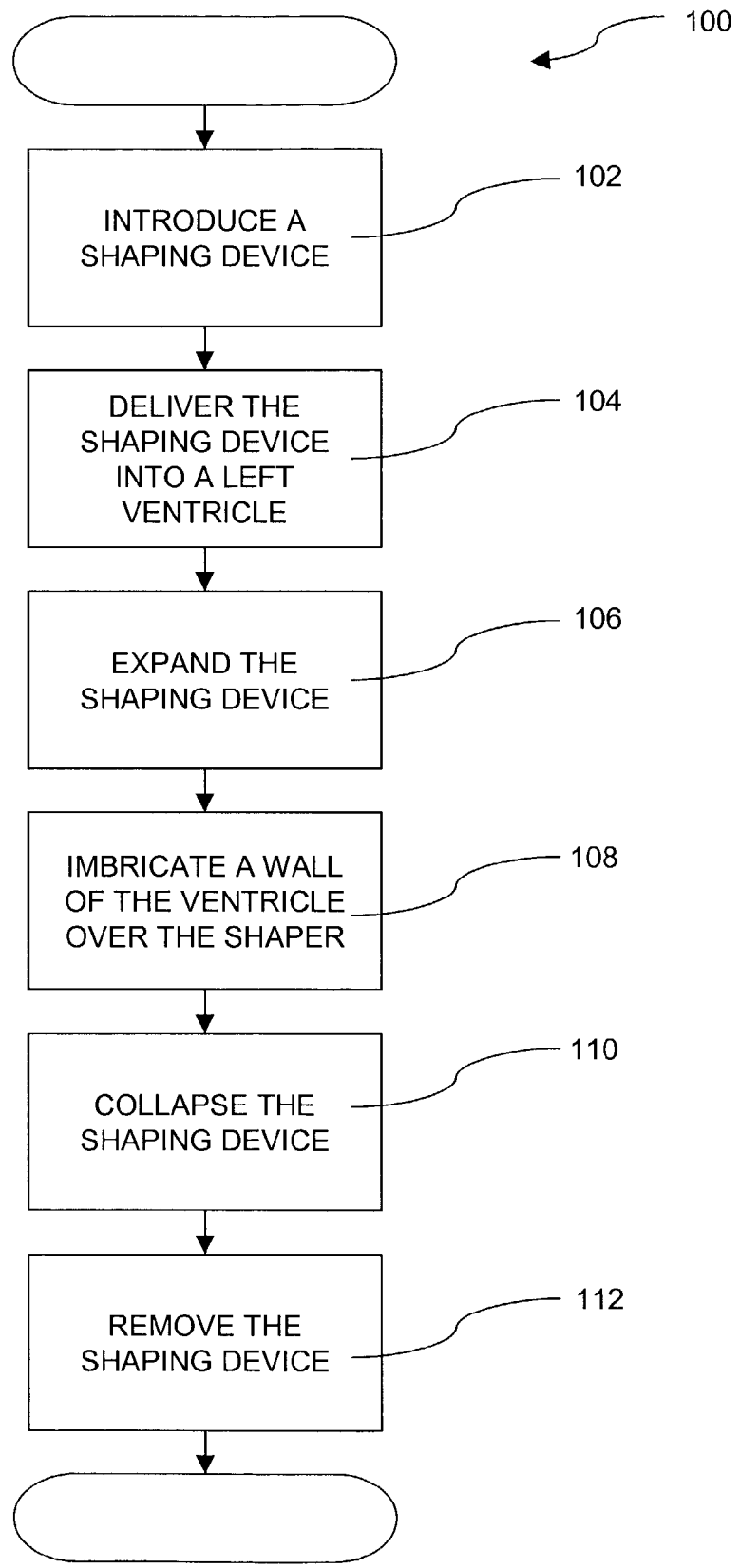

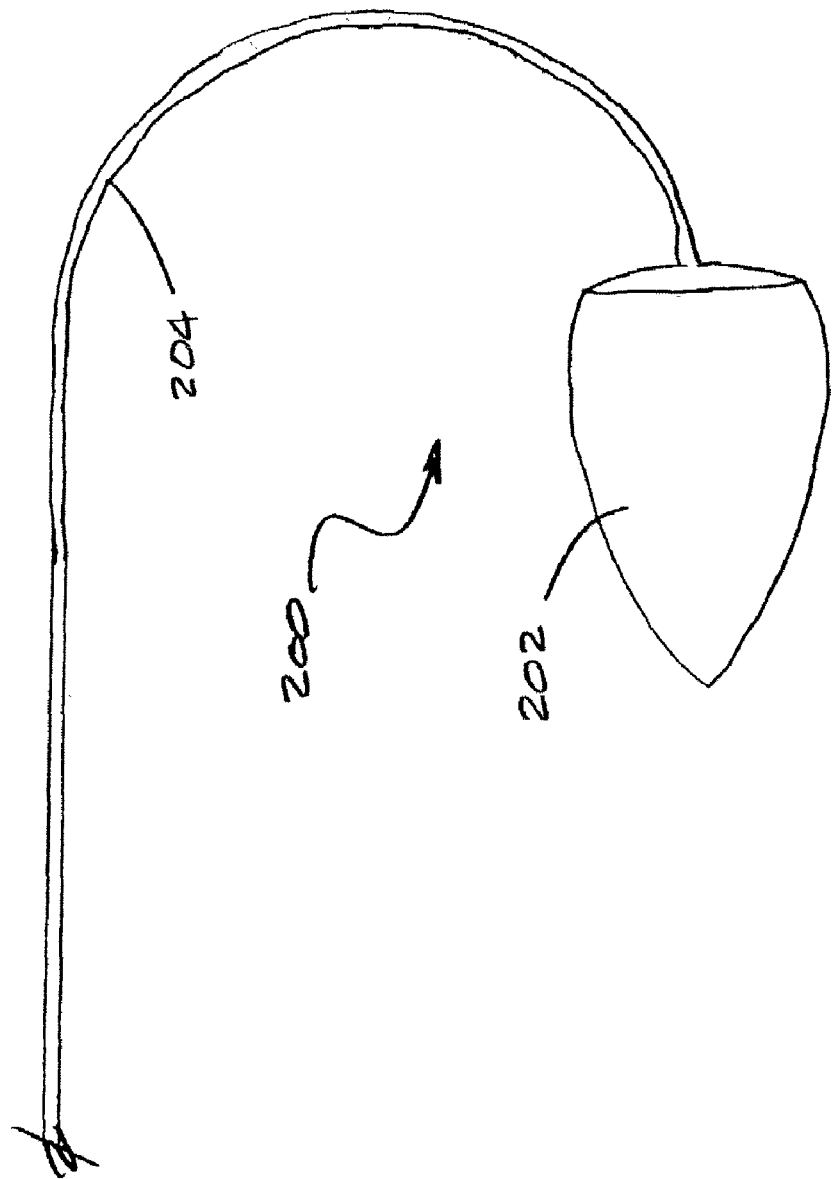

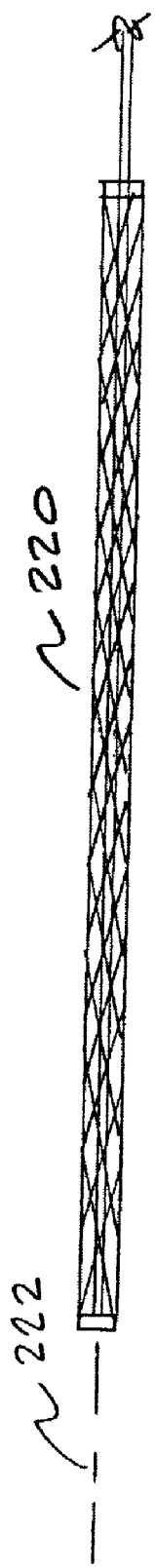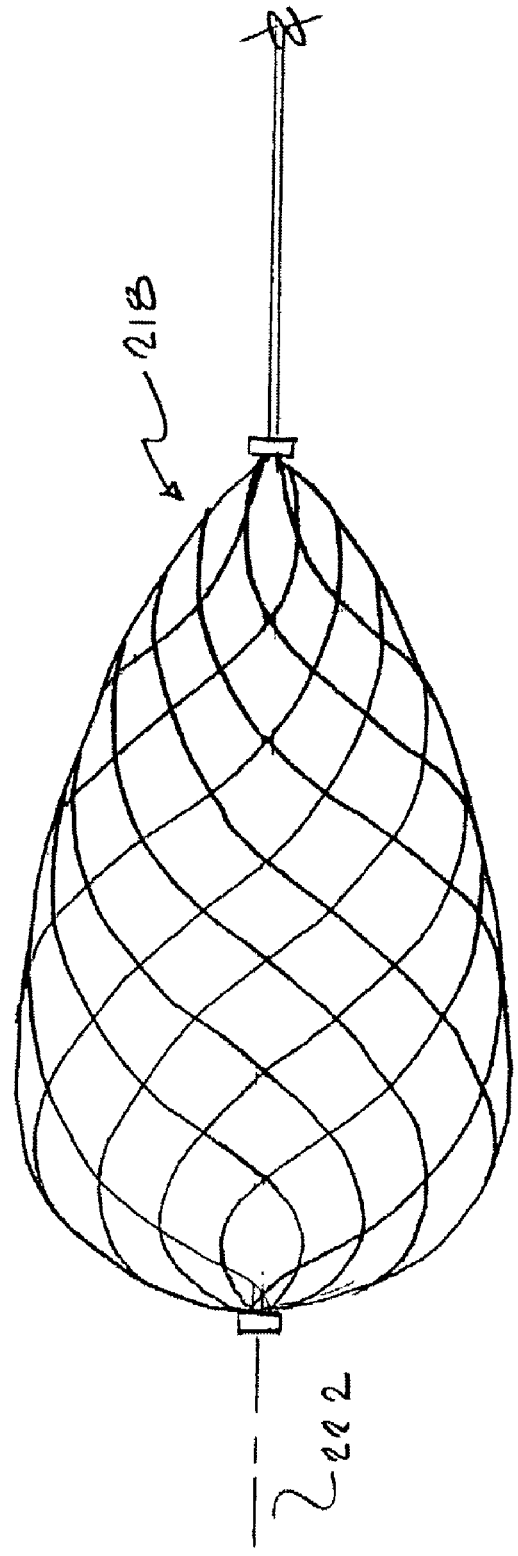
Fig. 2e
Fig. 2d

METHOD AND DEVICE FOR PERCUTANEOUS SURGICAL VENTRICULAR REPAIR

PRIORITY CLAIM

This application claims the benefit of the filing date of U.S. provisional patent application Ser. No. 60/317,197 entitled "DEVICE AND METHOD FOR ENDOSCOPIC SURGICAL VENTRICULAR REPAIR" filed on Sep. 5, 2001 and U.S. provisional patent 60/327,221 entitled "METHOD AND DEVICE FOR CLOSED CHEST PLACEMENT OF SEPTUM" filed on Oct. 5, 2001, the disclosures of both of these applications are incorporated herein by reference.

BACKGROUND OF THE INVENTION

1. Field of the Invention

This invention relates generally to surgical methods and apparatuses for performing surgical ventricular repair endoscopically or through a minimally invasive incision.

2. Description of the Related Art

The function of a heart in an animal is primarily to deliver life-supporting oxygenated blood to tissue throughout the body. This function is accomplished in four stages, each relating to a particular chamber of the heart. Initially deoxygenated blood is received in the right auricle of the heart. This deoxygenated blood is pumped by the right ventricle of the heart to the lungs where the blood is oxygenated. The oxygenated blood is initially received in the left auricle of the heart and ultimately pumped by the left ventricle of the heart throughout the body. It can be seen that the left ventricular chamber of the heart is of particular importance in this process as it is relied upon to pump the oxygenated blood initially through a mitral valve into and ultimately throughout the entire vascular system.

The shape and volume of the normal heart are of particular interest as they combine to dramatically affect the way that the blood is pumped. The left ventricle which is the primary pumping chamber, is somewhat elliptical, conical or apical in shape in that it is longer, long axis longest portion from aortic valve to apex, than it is wide, short axis widest portion from ventricle wall to septum, and descends from a base with a decreasing cross-sectional circumference, to a point or apex. The left ventricle is further defined by a lateral ventricle wall and a septum, which extends between the auricles and the ventricles.

Two types of motion accomplish the pumping of the blood from the left ventricle. One of these motions is a simple squeezing motion, which occurs between the lateral wall and the septum. The squeezing motion occurs as a result of a thickening of the muscle fibers in the myocardium. This compresses the blood in the ventricle chamber and ejects it into the body. The thickening changes between diastole and systole. This is seen easily by echocardiogram, PET and MRI imaging and can be routinely measured.

The other type of motion is a twisting or writhing motion, which begins at the apex and rises toward the base. The rising writhing motion occurs because the heart muscle fibers run in a circular or spiral direction around the heart. When these fibers constrict they cause the heart to twist initially at the small area of the apex, but progressively and ultimately to the wide area of the base. These squeezing and twisting motions are equally important, as they are each responsible for moving approximately one-half of the blood pumped. The contractility or stiffness of these fibers are major determinants in how well the ventricle pumps.

The amount of blood pumped from the left ventricle divided by the amount of blood available to be pumped is referred to as the ejection fraction of the heart. Generally, a healthier heart has a higher ejection fraction. A normal heart, for example may have a total volume of one hundred milliliters and an ejection fraction of sixty percent. Under these circumstances, 60 milliliters of blood are pumped with each beat of the heart. It is this volume in the normal heart of this example that is pumped with each beat to provide nutrients including oxygen to the muscles and other tissues of the body.

Realizing that the heart is part of the body tissue, and the heart muscle also requires oxygenated blood, it can be appreciated that the normal function of the heart is greatly upset by clotting or closure of the coronary arteries. When the coronary arteries are blocked, an associate portion of the heart muscle becomes oxygen-starved and begins to die. This is clinically referred to as a heart attack. Ischemic cardiomyopathy typically occurs as the rest of the heart dilates in an attempt to maintain the heart's output to the body.

As the ischemia progresses through its various stages, the affected myocardium dies losing its ability to contribute to the pumping action of the heart. The ischemic muscle is no longer capable of contracting so it cannot contribute to either squeezing or twisting motion required to pump blood. This non-contracting tissue is said to be akinetic. In severe cases the akinetic tissue, which is not capable of contracting, is in fact elastic so that blood pressure tends to develop a bulge or expansion of the chamber. This muscle tissue is not only akinetic, in that it does not contribute to the pumping function, but it is in fact dyskinetic, in that it detracts from the pumping function. This is particularly detrimental to the limited pumping action available, as the heart loses even more of its energy to pumping the bulge instead of the blood.

The body seems to realize that with a reduced pumping capacity, the ejection fraction of the heart is automatically reduced. For example, the ejection fraction may drop from a normal sixty percent to perhaps twenty-percent. Realizing that the body still requires the same volume of blood for oxygen and nutrition, the body causes its heart to dilate or enlarge in size so that the smaller ejection fraction pumps about the same amount of blood. As noted, a normal heart with a blood capacity of seventy milliliters and an ejection fraction of sixty percent would pump approximately 42 milliliters per beat. The body seems to appreciate that this same volume per beat can be maintained by an ejection fraction of only thirty-percent if the ventricle enlarges to a capacity of 140 milliliters. This increase in volume, commonly referred to as "remodeling", not only changes the volume of the left ventricle, but also its shape. The heart becomes greatly enlarged and the left ventricle becomes more spherical in shape losing its apex.

On the level of the muscle fibers, it has been noted that dilation of the heart causes the fibers to reorient themselves so that they are directed away from the inner heart chamber containing the blood. As a consequence, the fibers are poorly oriented to accomplish even the squeezing action, as the lines of force become less perpendicular to the heart wall. This change in fiber orientation occurs as the heart dilates and moves from its normal elliptical shape to its dilated spherical shape. The spherical shape further reduces pumping efficiency since the fibers which normally encircle the apex facilitate writhing are changed to a more flattened formation as a result of these spherical configurations.

Of course, this change in architecture has a dramatic effect on wall thickness, radius, and stress on the heart wall. In particular, it will be noted that absent the normal conical shape, the twisting motion at the apex, which can account for as much as one half of the pumping action, is lost. As a consequence, the more spherical architecture must rely almost totally on the lateral squeezing action to pump blood. This lateral squeezing action is inefficient and very different from the more efficient twisting action of the heart.

Although the dilated heart may be capable of sustaining life, it is significantly stressed and rapidly approaches a stage where it can no longer pump blood effectively. In this stage, commonly referred to as congestive heart failure, the heart becomes distended and is generally incapable of pumping blood returning from the lungs. This further results in lung congestion and fatigue. Congestive heart failure is a major cause of death and disability in the United States where approximately 400,000 cases occur annually.

What is needed therefore is a reliable method and apparatus to allow a surgeon to perform surgical ventricular repair, preferably without having to do a full sternotomy and/or make large incisions in the chest. Additionally, such methods could be performed on a beating heart eliminating the need for lengthy full bypass circuit runs.

SUMMARY

In response to these and other problems, an improved apparatus and method is provided for endoscopic surgical ventricle repair which allows a surgeon to perform a surgical ventricular repair procedure through a closed chest or through a small thoracotomy on a beating, fibrillating or an arrested heart. In one embodiment, there is a method for repairing a heart of a human, comprising introducing a shaping device percutaneously into a vasculature of the human, wherein the shaping device is in a collapsed state, delivering the shaping device into a left ventricle through the vasculature, expanding the shaping device to an expanded shape, imbricating a wall of the ventricle over the shaping device, collapsing the shaping device, and removing the shaping device from the left ventricle such that the ventricle is restored to an appropriate size.

BRIEF DESCRIPTION OF THE DRAWINGS

FIG. 1—illustrates a process used by an embodiment.

FIG. 2a—illustrates an embodiment of a shaping device.

FIG. 2d—illustrates another embodiment of a shaping device in an expanded condition.

FIG. 2e—illustrates the embodiment of FIG. 2d in a collapsed condition.

DETAILED DESCRIPTION

Turning to FIG. 1, there is presented an overview method 100 for performing and using one embodiment. The method 100 may use the following components: a shaping device, a patch, and a stapling device.

The shaping device may be pre-shaped to generally model the appropriate volume and shape of the left ventricle, such as illustrated in FIG. 2a. Such a shaping device 200 may be used as a guide in reforming the left ventricle so that the reconstructed heart may be formed closer to the size and shape of the pre-enlarged heart. Consequently, the heart performs better post operatively than with conventional methods. As illustrated in FIG. 2a, the shaping device 200 is generally conical or "tear drop" in shape. The length of the shaping device 200 may vary with each patient and will typically be a function of the volume selected for the shaping device. Depending on the patient, the length may be in the three to four inch range to generally match the length of the pre-enlarged left ventricle. A doctor may select the appropriate volume for the shaping device by estimating the volume of the pre-enlarged left ventricle. Such selection procedures and shaping devices are discussed in a U.S. patent application Ser. No. 09/864,510, filed on May 24, 2001 by the inventors, which is hereby incorporated by reference into this application.

In some embodiments, such as illustrated in FIG. 2a, the shaping device may be an inflatable balloon 202 coupled to a filler tube 204. Such tubes are well known in the art, and illustratively may be made of plastic-type materials such as PVC. A proximal end of the filler tube 204 may be connected to a fluid reservoir (not shown) which may be used to fill a pre-specified amount of fluid into the balloon 202 through the filler tube 204. The injection of fluid through the filler tube 204 inflates the balloon 202 to an inflated condition.

Figure 2B:
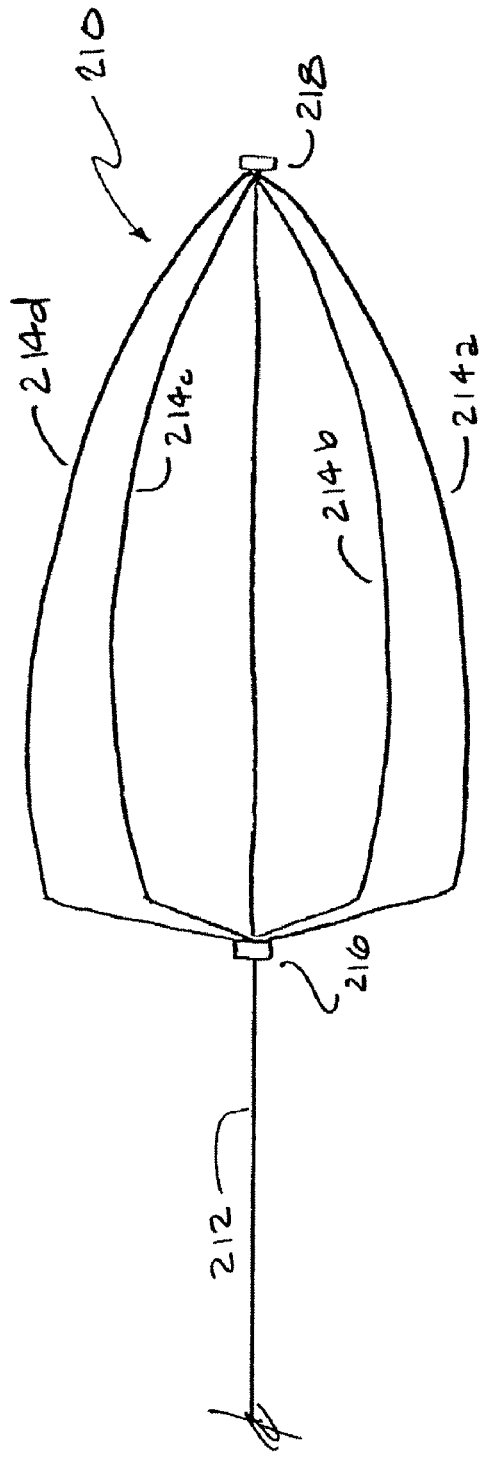
FIG. 2b—illustrates another embodiment of a shaping device in an expanded condition.

The shaping device could also be a wire skeleton or frame, as illustrated in FIG. 2b. The wire frame could be made from surgical grade stainless steel, titanium, tantalum, or nitinol, which is a commercially available nickel-titanium alloy material that has shape memory and is superelastic. Nitinol medical products are available from AMF of Reuilly, France, and Flexmedics Corp., of White Bear Lake, Minn.

The shaping device 210 illustrated in FIG. 2b is in an expanded condition. In this embodiment, a main wire 212 could run through the center of the shaping device 210. Coupled to the main wire may be a series of back ribs 214a though 214d. The back ribs 214a through 214d are coupled to a collar 216.

Figure 2C:
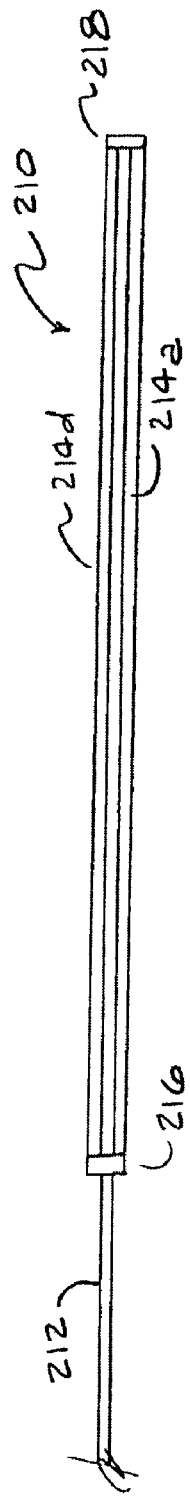
FIG. 2c—illustrates the embodiment of FIG. 2b in a collapsed condition.

FIG. 2c shows the shaping device 210 in a collapsed position. In a collapsed position, back ribs 214a-214d surround the main wire 212. In operation, once the shaping device 210 is inserted into the left ventricle, a doctor may cause the collar 216 to slide along the main wire 212 towards the distal end 218 of the wire. The force exerted on collar 216 will cause the ribs to buckle radially outward as illustrated in FIG. 2b to a predetermined shape.

Other embodiments may include a wire mesh system such as illustrated in FIG. 2d. The wire mesh shaper 218 is formed of a tubular fabric made from a plurality of wire strands having a predetermined relative orientation between the strands. Those skilled in the art will appreciate that the pick and pitch of the braided wires may be varied depending upon the desired density of the fabric. The tubular fabric may have metal strands which define two sets of essentially parallel generally spiraling and overlapping strands, with the strands of one set having a "hand", i.e. a direction of rotation, opposite that of the other set. This tubular fabric is known in the fabric industry as a tubular braid.

The pitch of the wire strands (i.e. the angle defined between the turns of the wire and the axis of the braid) and the pick of the fabric (i.e. the number of turns per unit length) as well as some other factors, such as the number of wires employed in a tubular braid, the size or diameter of each wire in the braid, and the diameter of the braid are all important in determining a number of important properties of the device. For example, the greater the pick and pitch of the fabric, and hence the greater the density of the wire strands in the fabric, the stiffer the device will be. Also, the greater the diameter of each wire of the braid, the stiffer the device will be.

The wire strands of the tubular metal fabric are preferably manufactured from so-called shape memory alloys. Such alloys tend to have a temperature induced phase change which will cause the material to have a preferred configuration which may be fixed by heating the material above a certain transition temperature to induce a change in the phase of the material. When the alloy is cooled back down, the alloy will "remember" the shape it was in during the heat treatment and will tend to assume that configuration unless constrained from so doing.

Without any limitation intended, suitable wire strand materials may be selected from a group consisting of a cobalt-based low thermal expansion alloy referred to in the field as ELGELOY, nickel-based high temperature high-strength "superalloys" (including nitinol) commercially available from, for example, Haynes International under the trade name HASTELLOY, nickel-based heat treatable alloys sold under the name INCOLOY by International Nickel, and a number of different grades of stainless steel. The important factor in choosing a suitable material for the wire strands is that the wires retain a suitable amount of the deformation induced by a molding surface when subjected to a predetermined heat treatment.

When the tubular braid, for example, is in its preformed relaxed configuration 218 as illustrated in FIG. 2d, the wire strands forming the tubular braid will have a first predetermined relative orientation with respect to one another. As the tubular braid is compressed along its axis 222, the fabric will tend to flare out away from axis 222 conforming to the shape of the mold. When the fabric is so deformed the relative orientation of the wire strands of the metal fabric will change. After undergoing the shape memory process, the resulting medical device has a preset relaxed configuration 218 as illustrated in FIG. 2d and a collapsed or stretched configuration 220 as illustrated in FIG. 2e which allows the device to be passed through a catheter or other similar delivery device.

In alternative embodiments, the shaping device may also have mechanisms by which the epicardium may be grabbed and conformed to the shape of the shaping device. As will be explained below, in such an embodiment, the clasping instrument may be placed along the outer surface of the ventricle at precise locations and closed to take a bite out of the ventricle, reshaping the ventricle around the shaping device.

A delivery device or catheter (not shown) may take any suitable shape, but desirably comprises an elongate flexible metal shaft having a threaded distal end. The delivery device may be used to urge the wire mesh shaper 218 through the lumen of a catheter for deployment in a channel of a patient's body. When the device is deployed out the distal end of the catheter, the device will still be retained by the delivery device. Once the wire mesh shaper 218 is properly positioned, the distal end of the catheter may be pressed against the medical device and the metal shaft or guidewire can be rotated about its axis to unscrew the medical device from the threaded distal end of the shaft. The catheter and guidewire are withdrawn.

As will be explained below, a patch is also used in the method 100. In one embodiment, the patch may be made from sheet material and may be a variety of shapes, including circular, elliptical, or triangular in shape. The sheet material for the patch may be formed from a biocompatible synthetic material, for example, from polyester, Dacron (Hemoshield) manufactured by the DuPont Corporation, or polytetrafluoroethylene (Gortex). The sheet material may also be autologous pericardium, or some other fixed mammalium tissue such as bovine pericardium or porcine tissue. The biocompatible synthetic material patch may be collagen impregnated to assist in hemostasis, or it may be sprayed with a hemostatic sealant to achieve better and instantaneous hemostasis.

On one side of the patch, there may be a means of adhering the patch to the endocardium or inside of the heart. Additionally, the patch may have markings that enable the movement and position of the patch to be post-operatively observed and analyzed under imaging systems, such as Magnetic Resonance Imaging ("MRI"), x-ray machines, fluoroscopy or other external visualization methods, for post-operative clinical evaluation. Such markings will allow identification of the patch and allow for analysis of the heart's contractility in future post-operative evaluations. The markings may also be radiopaque. Such radiopaque markings are discussed in U.S. patent application Ser. No. 09/864,510, filed on May 24, 2001 by the inventors, which has been incorporated by reference into this application.

In some embodiments, the shaping device may be coupled to the patch or have a mechanism, which couples to and releases the patch.

An imaging system may also be used preoperatively to take MRI, PET or echocardiography imaging data of the ventricle to determine what the appropriate areas of the ventricle to exclude are and to determine what the appropriate volume of the ventricle should be.

Turning back now to FIG. 1, the method 100 will now be discussed. For purposes of illustration only and not by way of limitation the method 100 will now be discussed as part of a bypass procedure. The procedure may begin by the surgeon positioning an endoscopic camera into the patient to view the infracted area of the patient's heart. Preoperatively, the surgeon may determine the size of the shaping device by selecting a shaping device that matches the volume of the ventricle desired for the particular patient.

When the shaping device is in a collapsed state, in 102, the shaping device may be introduced into the vasculature or vascular system of the patient. From the vascular system, in 104, the shaping device is guided into the left ventricle.

Figure 3A:
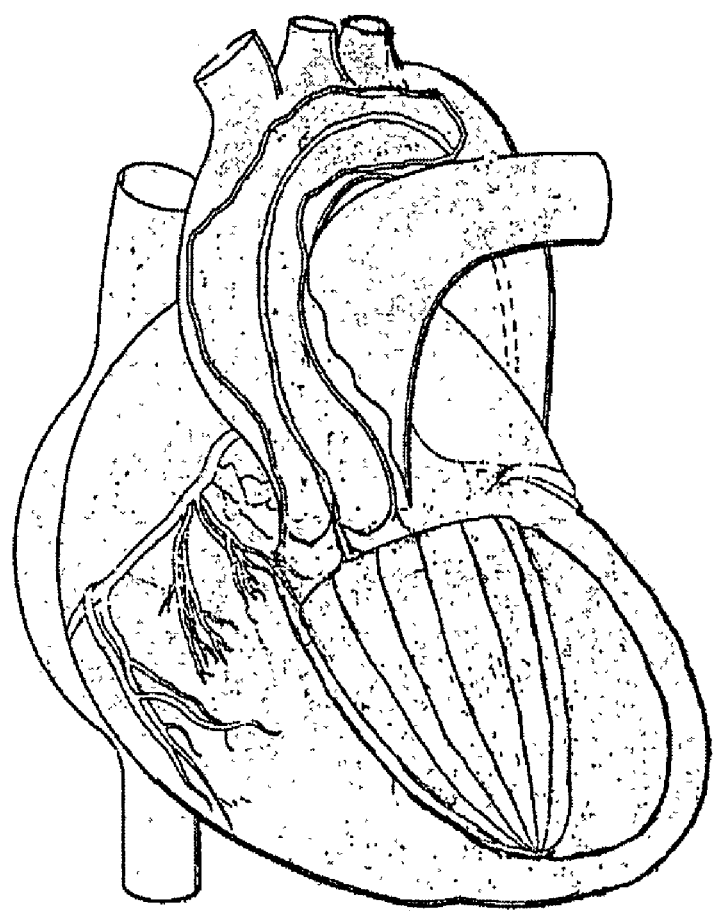
FIG. 3a—illustrates one embodiment deployed within a human heart.

In a bypass procedure, the femoral vein and artery are cannulated to connect the patient to the cardiopulmonary bypass machine. After the bypass machine is running, the shaping device is manipulated to deploy from a collapsed state to an expanded shape. In some embodiments, markings on the controlling handle will provide feedback to the surgeon on how the shaping device is positioned, so that he knows where the patch is in relation to the ventricle. A positioning device on the shaping device will align with an anatomical landmark inside the ventricle, like the aortic annulus, to provide another reference location for the shaping device. In 106, the shaping device may be deployed into an expanded condition, as shown in FIG. 3a.

Figure 3B:
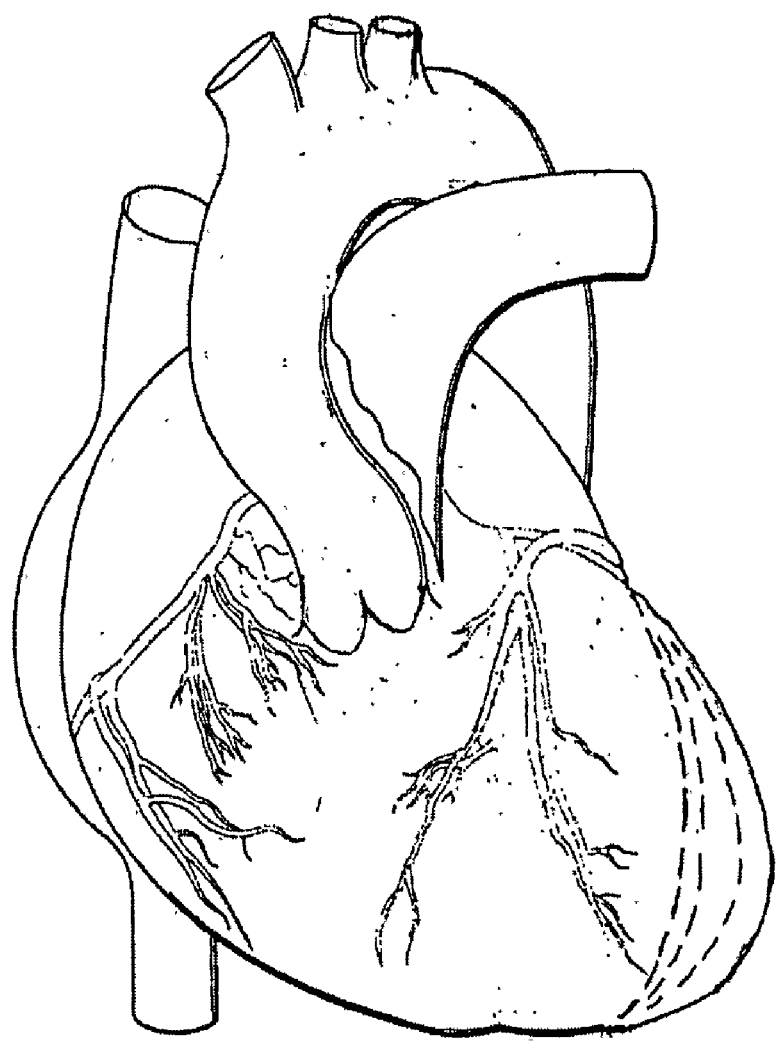
FIG. 3b—illustrates a human heart before remodeling.

In 108, the wall of the ventricle may be imbricated over the shaping device, as shown in FIG. 3b. The term "imbricating" as used in this application means to bring together two edges of the ventricle wall that have non-viable tissue between them and excluding this portion of the ventricle wall will which will basically reshape the ventricle. The shaping device may help determine which edges should be brought together. However, some non-viable tissue may be left in the ventricle in order to reshape the ventricle to the appropriate size and shape.

In order to imbricate or reform the ventricle wall over the shaping device, a molding instrument may be inserted into the chest through a small opening in an intercostal space to reach the epicardium. This molding instrument will allow the surgeon to press the ventricle wall against the shaping device to help reshape the ventricle, as shown in FIG. 3b. This molding instrument will be withdrawn and a clasping instrument may be inserted. The molding instrument and clasping instrument may be one device. This clasping device will take portions or "bites" out of the ventricle wall starting at the edges of the area of non-viable tissue that needs to be excluded to restore the ventricle to its correct shape, size and contour. The bites may be made with suture type devices, stapling devices, or clip type devices, for example. The clasping instrument may be partially closed to allow the surgeon to ensure that he is properly shaping the ventricle onto the shaping device. If the surgeon determines that he has the clasping instrument placed properly, the device will allow for full closure. The implements placed by the clasping instrument when closed will have pulled the ventricle wall over the shaping device and will maintain the ventricle's shape. Turning back to FIG. 1, once the shaping is complete, in 110, the shaping device will be collapsed and removed from the ventricle (112). Additionally, intraoperative imaging may be used during this procedure to aid the surgeon's view of the mandrel and ventricle interface.

Figure 4:
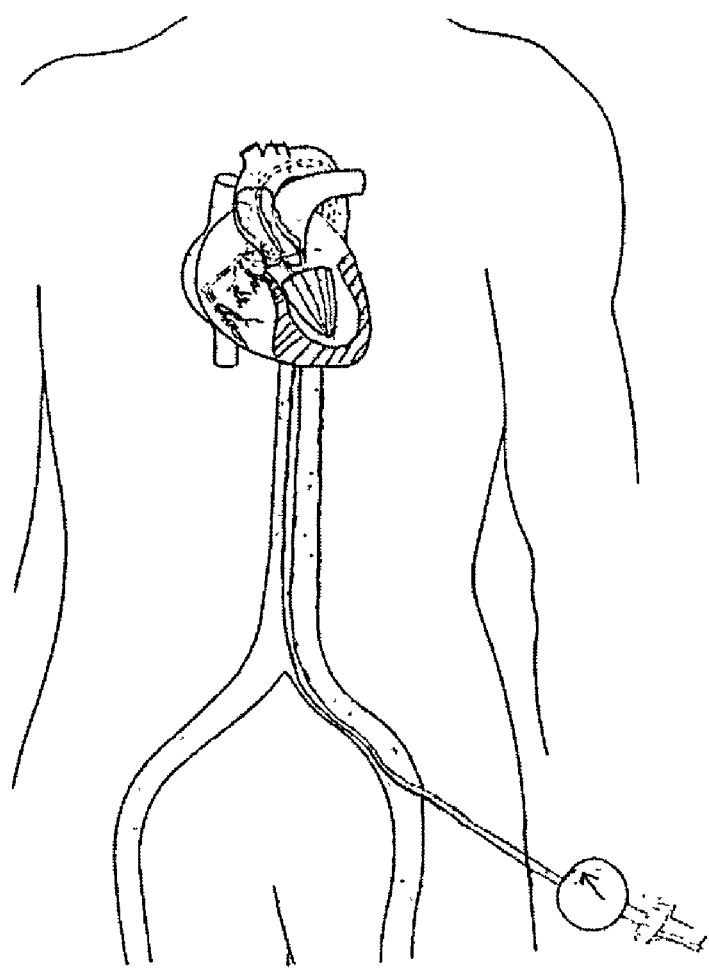
FIG. 4—illustrates one embodiment deployed within a human heart.

Alternatively, the method 100 may be performed on a beating heart. Referring back to 102 of FIG. 1, the collapsed shaping device may be inserted into a femoral artery. In 104, the shaping device is passed through the femoral artery to the left ventricle as illustrated in FIG. 4. Once in the ventricle the shaping device is expanded briefly and the surgeon checks the alignment indicators to ensure that the patch is in the correct position. He collapses the mandrel and allows the heart to beat normally. This procedure minimizes the heart's contractions for a very brief period of time while the shaping device is deployed, but allows the heart to beat when the shaping device is collapsed. Once the surgeon has determined that the patient may tolerate another low flow period, the shaping device will be expanded again (106), and the wall of the ventricle is imbricated over the shaping device (108). The imbrication is performed with the placement of clasping mechanisms. The placement of the clasping mechanisms may be determined from analysis of the preoperative imaging. A small opening is made in an intercostal space and the clasping device is placed through this opening. Clasping mechanisms are now placed on the ventricle and partially closed. The shaping device is deployed again briefly and the surgeon assesses the progress of the procedure and collapses the shaping device. If the clasping mechanisms are in the correct position the shaping device is expanded again and the clasping mechanisms are closed fully. The deployed shaping device ensures that the ventricle is of the intended volume. In 110, the shaping device is collapsed and removed from the ventricle and the femoral artery (112).

The method 100 could also be done as part of a thoracotomy, where the chest is opened in an intercostal space to allow greater access to the ventricle. The surgeon could use the intercostal space opening to position the clasping instrument. If the surgeon chooses, he could do revascularization of the lateral anterior descending artery along with the procedure. A cannula may be placed in the jugular vein to deliver cardioplegia to the coronary sinus, if the surgeon desires to do the anastomosis on an arrested heart.

Figure 5:
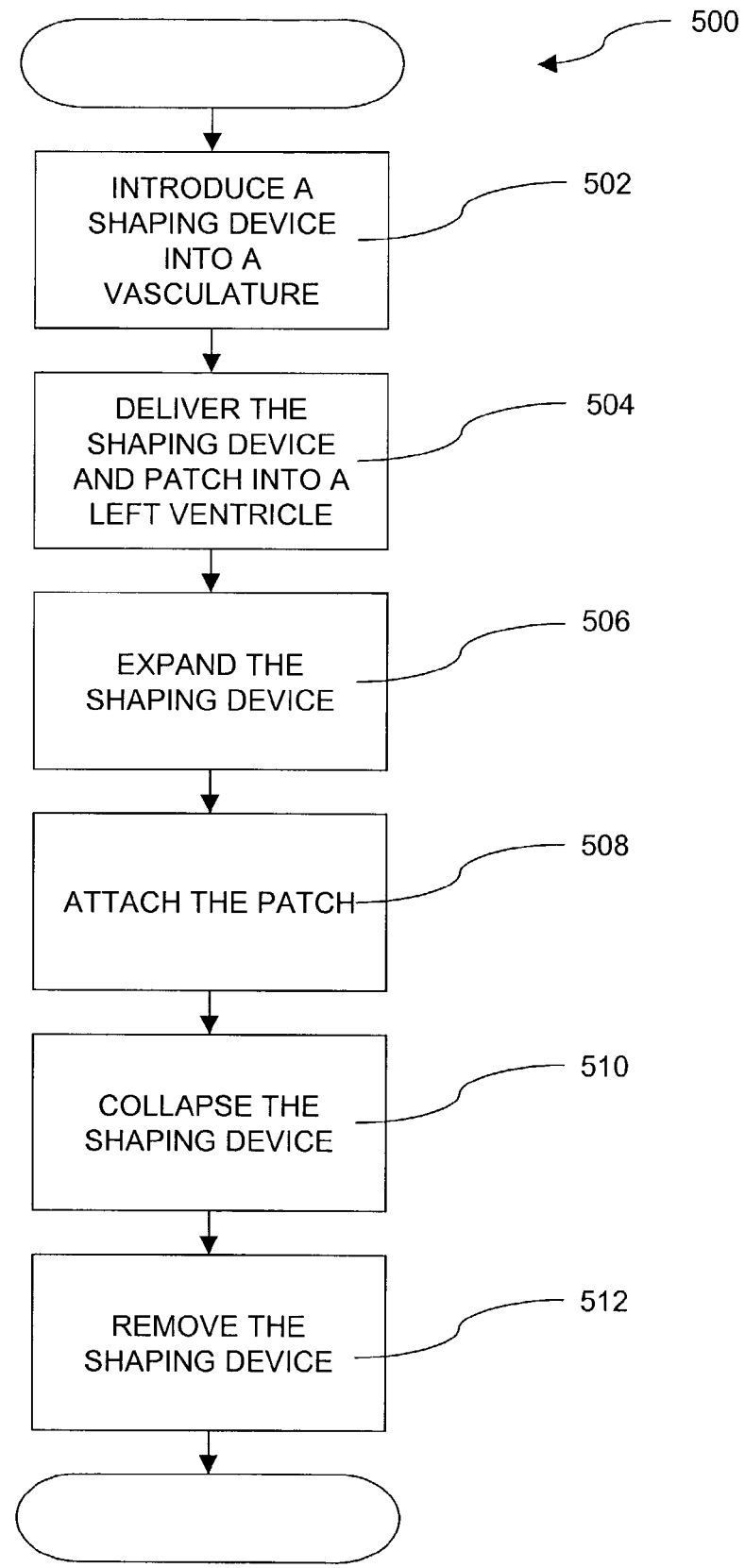
FIG. 5—illustrates a process.

Turning to FIG. 5, a method 500 will now be discussed. The method 500 may be used as either part of a bypass procedure or a beating heart procedure. As discussed in relation to method 100, the surgeon may determine the location of the ventricle to be excluded (i.e., "the excluded portion"). Thus, the surgeon may cut a patch to a size that covers the excluded portion or select a presized patch to match the excluded portion. Alternatively, the patch may also be a predetermined size that corresponds to the size of the shaping device and where the patch would be preattached to the shaping device. Once the size of the patch has been determined, the surgeon selects a shaping device that matches the volume of the ventricle desired for the particular patient. In one embodiment, the patch is secured to the shaping device and the shaping device is collapsed into/onto a delivery catheter.

When the shaping device is in a collapsed state, in 502 the shaping device and patch may be introduced into the vasculature or vascular system of the patient. From the vascular system, in 504, the shaping device and patch is guided into the left ventricle.

Figure 7:
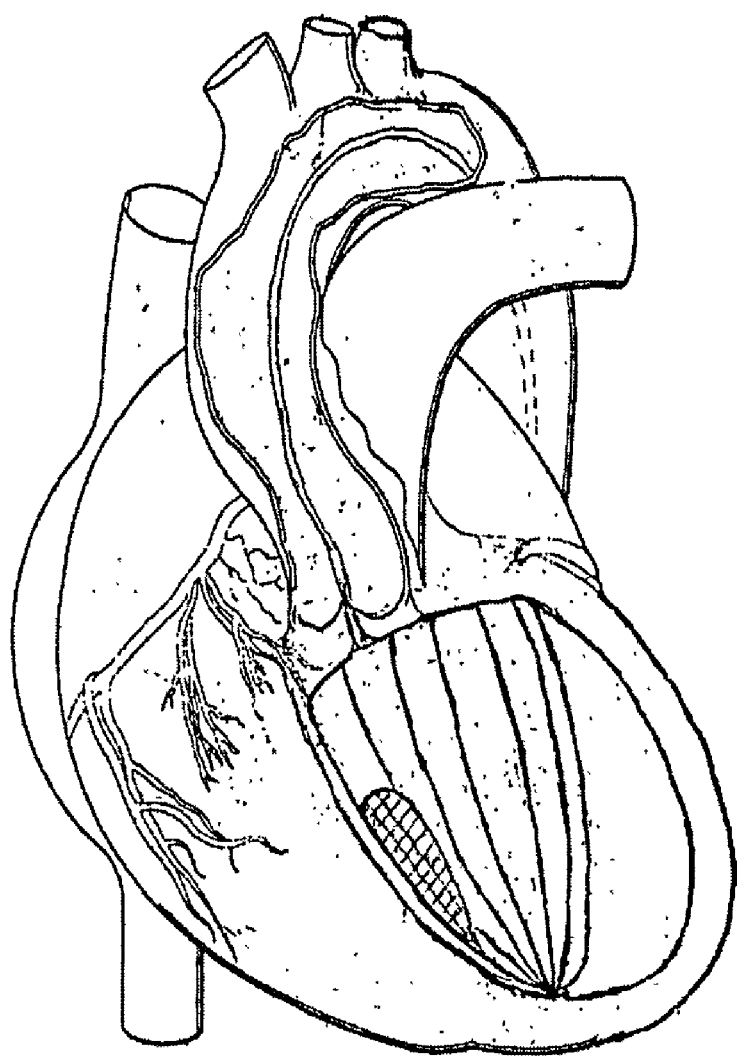
FIG. 7—illustrates one embodiment deployed within a human heart.

In some embodiments, markings on the controlling handle will provide feedback to the surgeon on how the shaping device is positioned, so that he knows where the patch is in relation to the ventricle. A positioning device on the shaping device will align with an anatomical landmark inside the ventricle, like the aortic annulus, to provide another reference location for the shaping device. In 506, the shaping device may be deployed into an expanded condition, as illustrated in FIG. 7.

Once the molding instrument has been deployed, in 508, the patch may be attached to the epicardium of the heart. Once the shaping is complete, in 510, the shaping device will be collapsed and removed from the ventricle (512).

Alternatively, the wall of the ventricle may be imbricated over the shaping device. In order to imbricate or reform the ventricle wall over the shaping device, a molding instrument may be inserted into the chest through a small opening in an intercostal space to reach the epicardium. This molding instrument will allow the surgeon to press the ventricle wall against the shaping device, to ensure that the patch gripping mechanism attaches to the ventricle wall that is to be excluded. This molding instrument will be withdrawn and a clasping instrument may be inserted. The molding instrument and clasping instrument may be one device. This clasping device may take portions or bites out of the ventricle wall starting at the edges of the area of non viable tissue that needs to be excluded to restore the ventricle to its correct shape, size and contour. The bites may be made with suture type devices or clip type devices, for example. The clasping instrument may be partially closed to allow the surgeon to ensure that he is properly shaping the ventricle onto the shaping device. If the surgeon determines that he has the clasping instrument placed properly, the device will allow for full closure. The implements placed by the clasping instrument when closed will have pulled the ventricle wall over the shaping device and will maintain the ventricle's shape. Intraoperative imaging may be used during this procedure to aid the surgeon's view of the mandrel and ventricle interface.

Similarly, the method 500 may be performed on a beating heart using intraoperative imaging. The shaping device, with the patch attached, may be passed through a femoral artery to the left ventricle. Once in the ventricle the shaping device is expanded and an image is made of the ventricle and the shaping device is collapsed. This stops the heart for a very brief period of time while the shaping device is deployed, but allows the heart to beat when the shaping device is collapsed. Once the image is analyzed to ensure that the patch is in the proper place, the shaping device will be expanded again and the patch secured with the assistance of the molding instrument and the shaping device collapsed. The placement of the clasping mechanisms on the clasping device is done from analysis of the preoperative imaging. A small opening is made in an intercostal space and the clasping device is placed through this opening. Clasping mechanisms are now placed on the ventricle and partially closed. The shaping device is deployed again and another image taken of the ventricle and the shaping device collapsed. This image is analyzed to ensure that the positioning of the clasping mechanisms is creating the desired shape of the ventricle over the shaping device. If the clasping mechanisms are in the correct position the shaping device is expanded again and the clasping mechanisms are closed fully. The deployed shaping device ensures that the ventricle is the correct volume. The shaping device is collapsed and withdrawn from the ventricle and the femoral artery.

Another alternative is to place the patch into the ventricle separately from the shaping device. This procedure may be accomplished by having the patch introduced into the ventricle with a catheter across the aortic valve and secured in a fashion similar to the method 500. The patch could also be placed across the septal wall from the right ventricle. In this embodiment a cannula is advanced into the right ventricle and a small hole is made in the septum between the right and left ventricles. Another cannula with the proper shaped patch is advanced into the right ventricle and through the hole in the septum where one half of the patch is deployed. The cannula is pulled back into the right ventricle where the second half of the patch device is deployed. The deployment of the patch on both sides of the ventricle holds the patch securely in place.

In yet another alternative procedure, the patch may be placed on the shaping device and introduced into the ventricle. The patch is attached to the wall of the ventricle and a device on the patch is tightened to cause the patch to reshape the ventricle over the shaping device. Once the desired shape is achieved the shaping device is removed and the patch left in place to hold the desired shape.

Figure 6:
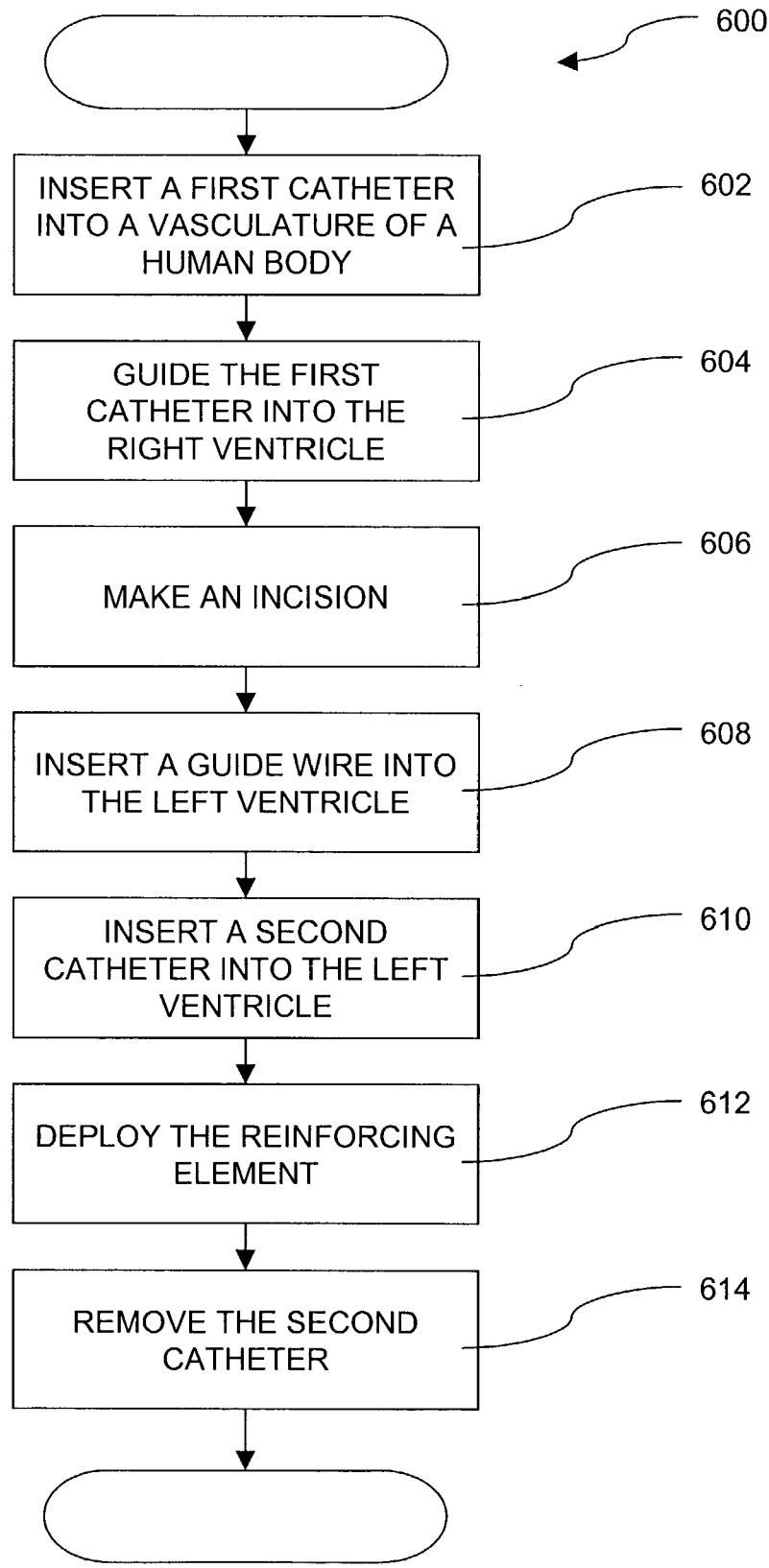
FIG. 6—illustrates a process.

Turning now to FIG. 6, there is one embodiment for a method of reinforcing a dilated portion of an endocardial surface of a human heart. In this embodiment, a surgeon preoperatively determines the location, size and shape of the area of the septum to be reinforced. The surgeon determines which appropriate reinforcing element will match the patient needs. Such reinforcing elements may be made from biocompatible materials and may take many forms. For instance, a patch material (discussed above) could be used. Such materials could be encapsulated within a deploying and securing mechanism that would allow them to be attached to the septal wall. Another example of a reinforcing element could be a device made from shape memory metal that has the shape of the area to be reinforced and has biocompatible material covering the metal framework. As discussed above, the metal frame could be made of memory shape materials and would provide a means to secure the material and the material would give substance to the metal frame to resist the pressure in the left ventricle. Additionally, the reinforcing element may also have radiopaque markings in a pattern that allow them to be viewed and analyzed postoperatively and may have a shape that matches the area to be reinforced. The reinforcing element may be shaped to match the patient anatomy and extent of injury. The securing device may have a mechanism by which the reinforcing element may be secured to the septum along the border zone between viable and non-viable tissue. In yet another embodiment, the reinforcing element could have a first surface and a second surface, where the first surface is adapted to match the dilated portion of the endocardium, and the second surface is adapted to match an appropriate shape of the left ventricle. Thus, the reinforcing element could also be used to reshape the ventricle.

Figure 8A:
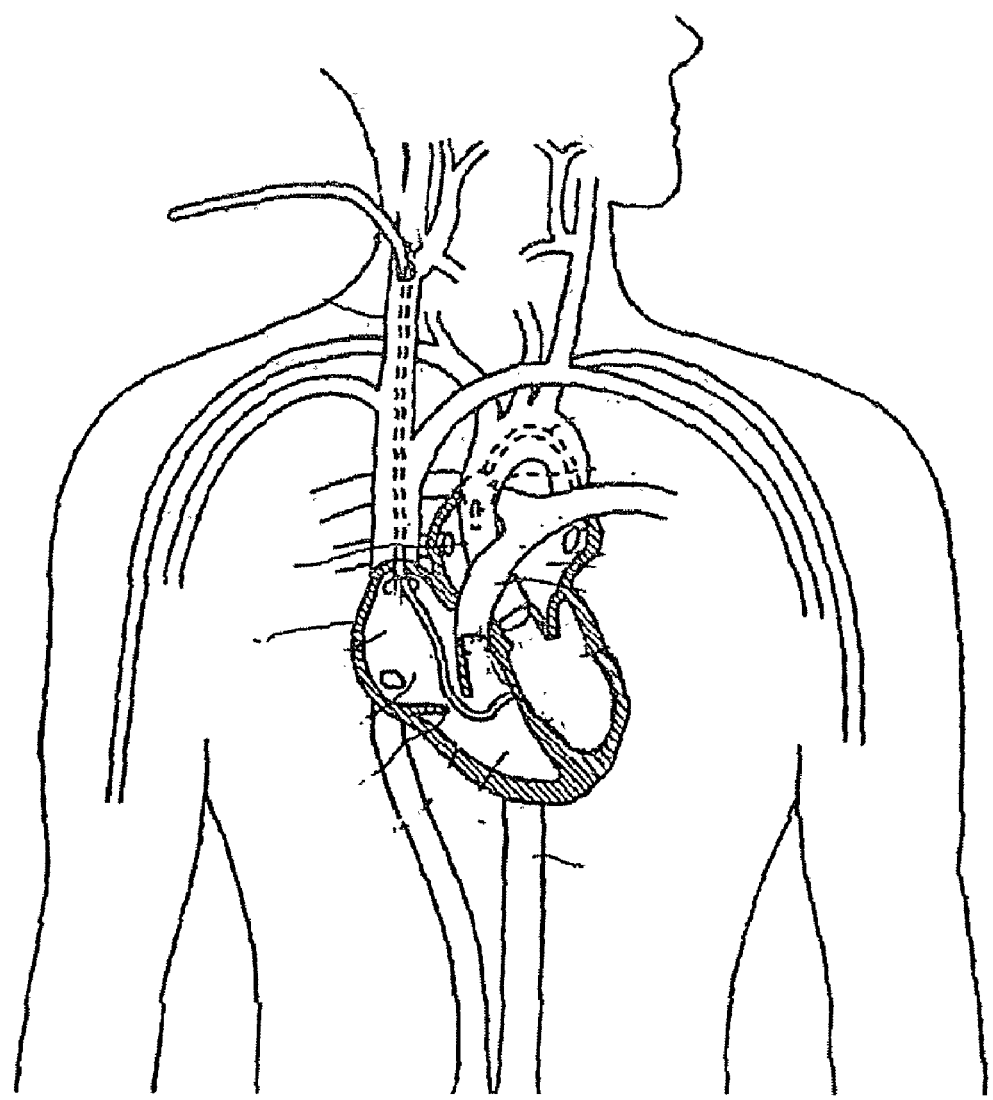
FIG. 8a—illustrates one embodiment deployed within a human heart.

Turning back to FIG. 6, in 602, the surgeon inserts a first catheter with a distal and proximal end percutaneously into a vasculature or vascular system (such as the jugular vein or the femoral vein) of the patient. The surgeon may route a guidewire through vein into the right ventricle in the vicinity of the area to be reinforced. With the guide wire in place, in 604, the surgeon may guide the first catheter into the right ventricle, as illustrated in FIG. 8*a*. Once the first catheter is in place, in 606, an incision may be made into the septal wall. In one embodiment, this may be accomplished with the aid of a trocar. The trocar may be advanced along the guide wire and positioned at the point in the septum that is generally the central point of the thinned septal region. The trocar is pushed through the thinned septal wall to create a path between the right and left ventricles.

Figure 8B:
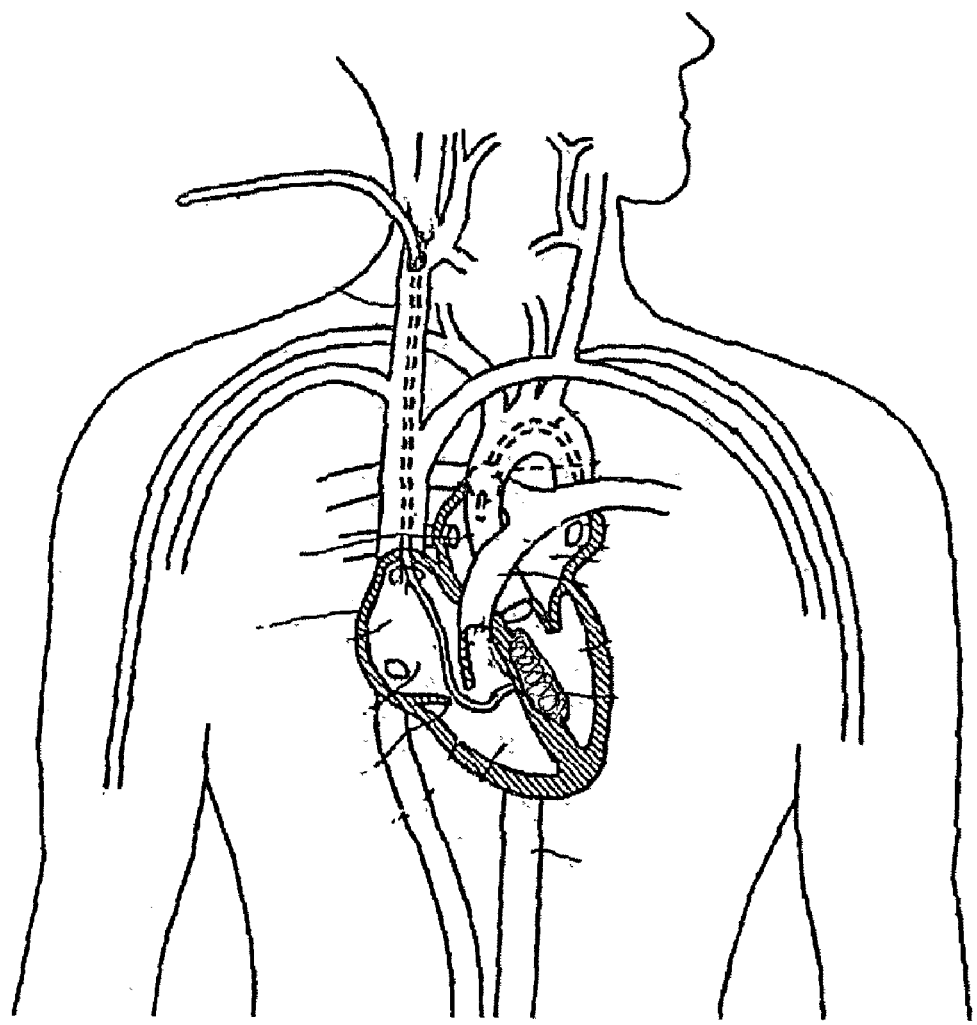
FIG. 8b—illustrates one embodiment deployed within a human heart.
Figure 8C:
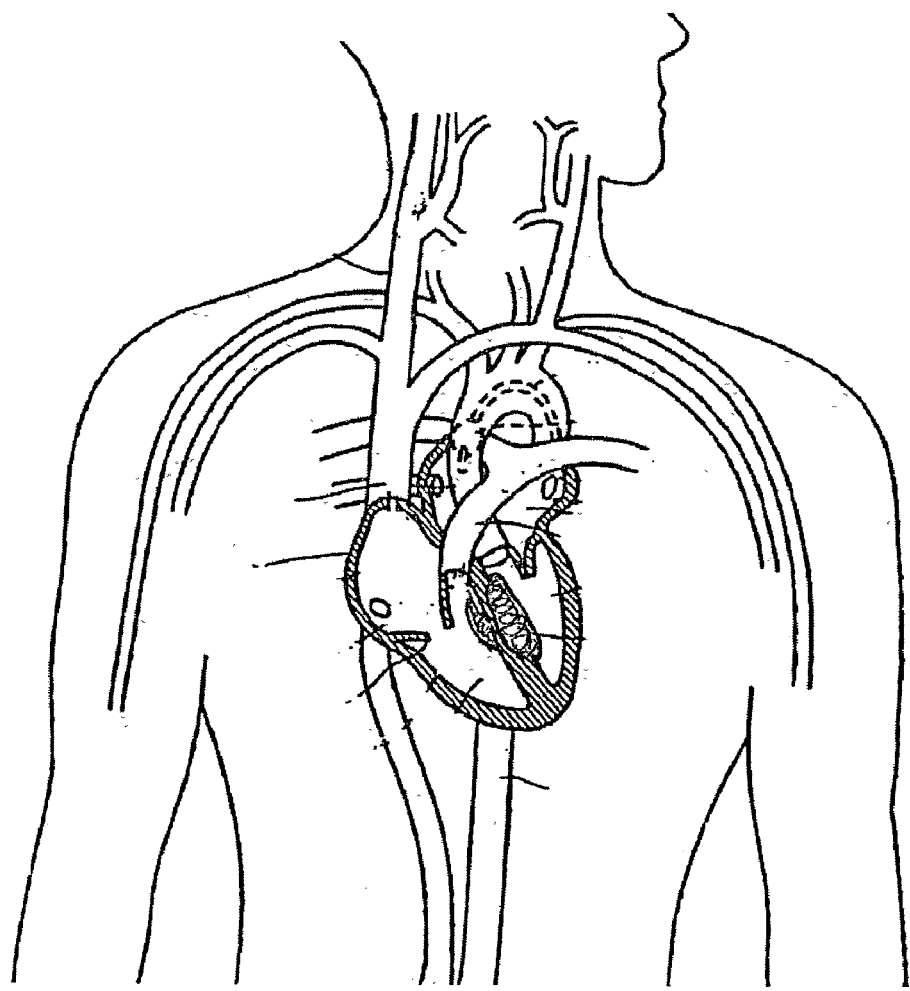
FIG. 8c—illustrates one embodiment deployed within a human heart.
Figure 8D:
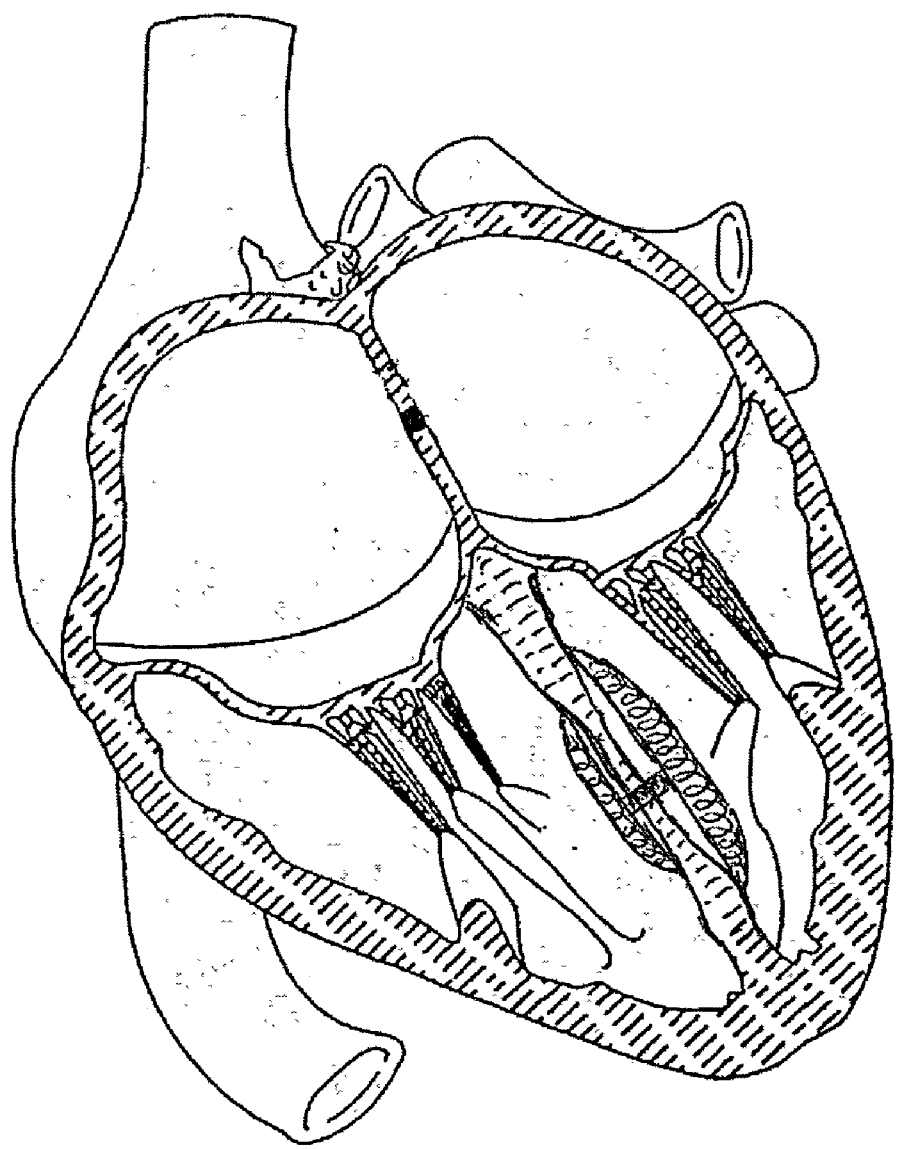
FIG. 8d—illustrates one embodiment deployed within a human heart.

In 608, the guidewire is advanced into the left ventricle from the right ventricle and, if a trocar is used, it may be withdrawn. In 610, a second catheter may be inserted over the guidewire such that the second catheter is introduced into the left ventricle. However, the second catheter is coupled to a reinforcing element, as described above. In 612, the reinforcing element is deployed in order to reinforce the portion of the endocardial surface, as illustrated in FIG. 8*b*. For instance, in the left ventricle side of the septum, one portion of the reinforcing element is deployed with the edges of the device and securing mechanism resting on viable tissue of the septum at the border zone of the non-viable septal tissue. A second part of the securing mechanism is deployed in the right ventricle and secured to the septal wall, as illustrated in FIGS. 8*c* and 8*d*. A securing mechanism could be a type of mechanism used to occlude ventricular septal defects. NMT Medical (Massachusetts), W.L. Gore (Arizona) and AGA Medical Corporation (Minnesota) manufacture such devices. In 614, all components are withdrawn from the right ventricle and the procedure is complete.

Alternatively, the method 600 could include inserting a patch into the left ventricle using the reinforcing element. The patch could be positioned such that the patch aligns with a non-viable region in the heart. The reinforcing element is expanded to an expanded shape. In the expanded shape the patch may be attach to the dilated portion of the heart. Additionally, the expanding could anchor the reinforcing element to the septal wall in the right ventricle.

Another embodiment may be where the reinforcing element and securing mechanism are deployed on either side of the ventricle without creating a hole in the septum. In this embodiment a guidewire would be placed in the jugular or femoral veins and advanced to the proper location at the septum. The reinforcing element and securing mechanism may be advanced along the guidewire and the reinforcing element secured to the septum at the border zone of the non-viable septal tissue. The securing mechanism may be secured to the viable tissue at the edge of the border zone. An example of a type of securing mechanism that may be used are those similar to securing devices used to secure thoracic aortic aneurysm grafts. Medtronic (Minnesota), W.L. Gore (Arizona) and Boston Scientific (Massachusetts) make these securing mechanisms. In this embodiment the reinforcing element could also be placed in the left ventricle side of the septum. The guidewire may be advanced through the aortic valve from the femoral artery or through one of the three great vessels coming off the aortic arch. The reinforcing element may be placed in a fashion similar to that used to place the device on the right ventricle side of the septum.

Another embodiment could have two reinforcing elements being placed on either side of the septum in both the right and left ventricles without being connected through the septum. The placement of both reinforcing elements would be done as described for the individual placements in the right and left ventricles.

This procedure could also be done as part of an endoscopic surgical ventricular repair, when the ventricle wall as well as the septum have been damaged due to ischemia. The placement of the reinforcing element will be as described in one of the methods above. The endoscopic surgical ventricular repair procedure consists of inserting a ventricular shaping device into the left ventricle via the femoral artery. A molding instrument may be inserted into the chest through a small opening in an intercostal space to reach the epicardium. This instrument will allow the surgeon to press the ventricle wall against the shaping mandrel, to ensure that ventricle is pressed against the mandrel. This pressing device will be withdrawn and a clasping instrument may be inserted. The molding instrument and clasping instrument may be one device. This device will take bites out of the ventricle wall starting at the edges of the area of non viable tissue that needs to be excluded to restore the ventricle to its correct shape, size and contour. The bites may be made with suture type devices or clip type devices, for example. Such devices are currently used in an endoscopic surgery procedure and commonly referred as GIA. In which a portion of the patient's stomach is excluded from the remainder of the stomach. These devices are manufactured by USSC (Connecticut), and Ethicon Endosurgery (Ohio). The clasping instrument may be partially closed to allow the surgeon to ensure that he is properly shaping the ventricle onto the shaping mandrel. If the surgeon determines that he has the clasping instrument placed properly the device will allow for full closure. The implements placed by the clasping instrument when closed will have pulled the ventricle wall over the shaping mandrel and will maintain the ventricle's shape. Once the shaping is complete, the shaping mandrel will be collapsed and taken from the ventricle. Intraoperative imaging may be used during this procedure to aid the surgeon's view of the mandrel and ventricle interface.

If needed, revascularization during the beating heart method may be done either with stents alone or with a LIMA to LAD graft using a small thoracotomy and stents on any other vessel that needs to be opened. All other aspects of surgical ventricular restoration may be performed.

It is further understood that other modifications, changes and substitutions are intended in the foregoing disclosure and in some instances some features of the disclosure will be employed without corresponding use of other features. Accordingly, it is appropriate that the invention be construed broadly and in a manner consistent with the scope of the disclosure.

The invention claimed is:

1. A method for repairing a heart of a human, the method comprising:
   introducing a shaping device percutaneously into a vasculature of the human, wherein the shaping device is in an at least partially collapsed state and is coupled to a patch,
   delivering the shaping device and patch into a left ventricle through the vasculature,
   positioning the shaping device such that the patch substantially aligns with at least a portion of non-viable tissue in the heart,
   expanding the shaping device to an expanded shape,
   attaching the patch to at least a part of the heart such that the ventricle is restored to an appropriate size,
   at least partially collapsing the shaping device, and
   removing the shaping device from the left ventricle.

2. The method of claim 1 further comprising substantially reforming the wall of the ventricle over the shaper.

3. The method of claim 2 further comprising excluding at least the portion of the non-viable tissue from the ventricle.

4. The method of claim 2 further comprising:
   opening the chest cavity, and
   securing the wall of the ventricle through the opening.

5. The method of claim 4 further comprising stapling the ventricle with a stapling instrument to secure the wall of the ventricle.

6. The method of claim 1 wherein the shaping device comprises a wire mesh structure, and further comprising expanding at least a portion of the wire mesh structure.

7. The method of claim 1 wherein the shaping device comprises a balloon, and further comprising expanding at least a portion of the balloon.

8. The method of claim 1 further comprising:
   assessing a size and shape for the patch, and
   cutting the patch to be of the assessed size and shape.

9. The method of claim 1, wherein the portion of non-viable tissue in the heart comprises akinetic tissue.

10. A method for reinforcing a human heart, comprising:
    introducing a securing mechanism percutaneously into a vasculature of a human body, wherein the securing mechanism is in an at least partially collapsed state;
    positioning the securing mechanism in the left ventricle such that a reinforcing element substantially aligns with at least a portion of non-viable tissue of the heart;
    coupling the reinforcing element to a part of the heart, wherein the reinforcing element is configured to inhibit expansion of the left ventricle beyond a predetermined volume;
    excluding at least a portion of the non-viable tissue from the ventricle; and
    removing the securing mechanism from the left ventricle.

11. The method of claim 10, further comprising expanding the securing mechanism.

12. The method of claim 10, further comprising collapsing the securing mechanism.

13. The method of claim 10, further comprising:
    assessing a size and shape for the reinforcing element; and
    modifying the reinforcing element to be the assessed size and shape.

14. The method of claim 10, wherein the securing mechanism comprises a shaping device.

15. The method of claim 14, wherein the securing mechanism comprises a wire mesh structure, and further comprising expanding at least a portion of the wire mesh structure.

16. The method of claim 14, wherein the securing mechanism comprises a balloon, and further comprising expanding at least a portion of the balloon.

17. A method of reinforcing a portion of an endocardial surface of a human heart, comprising:
    inserting a catheter with a distal and proximal end percutaneosly into a vasculature of a human body;
    guiding the catheter into a left ventricle;
    deploying a reinforcing element in order to reinforce the portion of an endocardial wall, wherein the reinforcing element is configured to substantially constrain the left ventricle to a predetermined maximum volume;

matching a first surface of the reinforcing element to a non-viable portion of the endocardium;

reforming the left ventricle to an appropriate shape and volume using a second surface of the reinforcing element; and removing the catheter from the left ventricle.

18. The method of claim 17, wherein the reinforcing element comprises a patch.

19. The method of claim 17, further comprising positioning the reinforcing element in the left ventricle using a securing mechanism.

20. The method of claim 17, further comprising:

assessing a size and shape for the reinforcing element, and modifying the reinforcing element to be the assessed size and shape.

21. The method of claim 19, further comprising:

positioning the securing mechanism such that at least a portion of the reinforcing element substantially aligns with a non-viable portion in the heart, expanding the securing mechanism to an expanded shape, and coupling the reinforcing element to a part of the heart.

22. The method of claim 17, wherein the reinforcing element comprises nitinol.

23. The method of claim 17, further comprising coupling the reinforcing element to the septal wall separating the left ventricle and a right ventricle.

* * * * *